United States Patent [19]

Tanabe

[11] 4,140,704

[45] Feb. 20, 1979

[54] PROCESS FOR PRODUCING CYCLIC ETHER

[75] Inventor: Yasuo Tanabe, Tokyo, Japan

[73] Assignee: Mitsubishi Chemical Industries Limited, Tokyo, Japan

[21] Appl. No.: 872,634

[22] Filed: Jan. 26, 1978

[30] Foreign Application Priority Data

Feb. 8, 1977 [JP] Japan .................................. 52-12673

[51] Int. Cl.² .......................................... C07D 307/08
[52] U.S. Cl. ............................................... 260/346.11
[58] Field of Search ..................................... 260/346.11

[56] References Cited

U.S. PATENT DOCUMENTS 4,005,113  1/1977  Smith .............................. 260/346.11
4,010,171  3/1977  Smith .............................. 260/346.11

FOREIGN PATENT DOCUMENTS 2415663  10/1975  Fed. Rep. of Germany.
1170222  11/1969  United Kingdom.

Primary Examiner—Richard Raymond
Attorney, Agent, or Firm—Bierman & Bierman

[57] ABSTRACT

This invention relates to an improved process for producing cyclic ether from an acetic acid ester of 1,4-glycol and water by cyclization reaction which is characterized by solidifying a high boiling by-product with or without a separation accelerator in the reaction residue, separating the solid obtained thereby from the residue of filtration and recycling a filtrate into the reaction zone.

19 Claims, 1 Drawing Figure

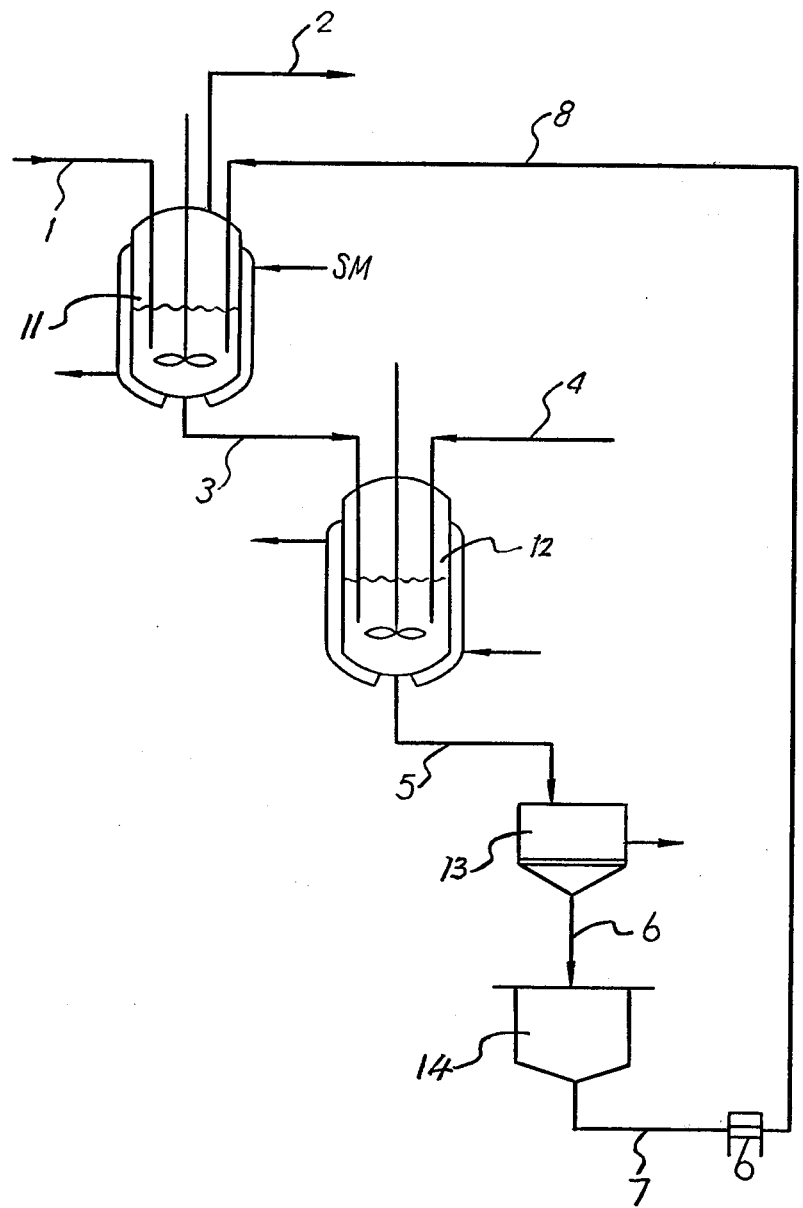

PROCESS FOR PRODUCING CYCLIC ETHER

BACKGROUND OF THE INVENTION

This invention relates to a process for the production of a cyclic ether directly from an ester of acetic acid and a 1,4-glycol. More particularly, the present invention is directed to an improved process for the production of tetrahydrofuran or dihydrofuran from an ester of acetic acid and 1,4-butanediol or 1,4-dihydroxybutene-2.

Tetrahydrofuran is useful as a solvent for various substances, especially as a solvent for high molecular weight substances such as polyvinyl chloride, polyvinylidene chloride and the like. A variety of processes have been hitherto known for the production of tetrahydrofuran, e.g. a process wherein furan obtained by decarbonylation of furfral is subjected to a catalytic hydrogenation, a process including hydrogenating a butynediol obtained by the reaction of acetylene with formaldehyde to form a butanediol product followed by dehydrative cyclization of the product, and a process including reacting 1,4-butanediol diacetate with water in the presence of an acid catalyst (Refer to British Patent No. 1,170,222).

In the production of a cyclic ether, especially tetrahydrofuran, from an ester of acetic acid and a 1,4-glycol, it is known to be advantageous to bring water in excess of the stoichiometric amount and in the form of steam, into a gas-liquid counter-current flow contact with the ester, because the cyclic ether is produced with high conversion rate and is recovered from the gas-liquid contacting zone as a gas phase (Refer to Offenlegungsshrift Nos. 2,415,663 and 2,456,780).

In this process, the reaction is performed in the presence of an acid catalyst. When a non-volatile, liquid acid catalyst is used, however, it is very difficult to prevent high boiling point by-products from being produced. The production of such high boiling point substances is very disadvantageous not only because it causes lowering of the yield of the cyclic ether but also because it necessitates complicated procedures at a distillation step for the recovery of the product and the catalyst. Moreover, these by-products have a tendency to deposite to the wall of a reaction vessel, resulting in the lowering of heat transmission efficiency of the reactor.

The present inventor has made many researches for developing processes for the production of a cyclic ether from an ester of acetic acid and a 1,4-glycol by the reaction with water in the presence of an acid catalyst. As a result of the researches, it has been found that high boiling point substances secondarily produced in the course of the cyclization reaction, can be easily solidified by a simple way and can be separated by filtration. The present invention is based on this finding.

SUMMARY OF THE INVENTION

It is an object of the present to provide an improved process for producing a cyclic ether from an acetic acid ester of 1,4-glycol and water by cyclization reaction in an industrially advantageous manner.

It is other object of the present invention to provide an improved process for producing cyclic ether, comprising separation step of a high boiling point substances by-product from a cyclization reaction medium.

It is another object of the present invention to provide an improved process for separating the high boiling point substance by-product from the cyclization reaction medium by solidifying said by-product with or without a separation-accelerator and filtering a solid thus produced.

It is further another object of the present invention to provide an improved process for producing cyclic ether, comprising separating a high boiling point substance by-product as a solidform by filtration and recycling a filtrate obtained thereby into the cyclization reaction zone.

The above-mentioned objects can be achieved according to the present invention summarized as follows.

In a process for the production of a cyclic ether by reacting an ester of acetic acid and 1,4-butanediol or 1,4-dihydroxybutene-2with water in the presence of non-volatile acid catalyst, an improved process characterized by the steps of:

(a) feeding both said ester and said acid catalyst as a liquid phase to a reaction zone and simultaneously feeding water thereto to allow the reaction between said ester and water to proceed;

(b) distilling off the cyclic ether produced in the reaction zone as a gas phase to leave a residue containing an unreacted ester, said acid catalyst and a high boiling substance in suspension or solution;

(c) discharging said residue from the reaction zone and introducing, after being mixed with water in order to promote a solidification of a high boiling substance with or without a separation-accelerator, said residue into a solid-liquid separation zone to separate said residue into a liquid phase portion and a solid phase portion; and (d) recycling said liquid phase portion into the reaction zone and withdrawing said solid phase portion from the separation zone.

BRIEF DESCRIPTION OF THE DRAWING

The sole FIGURE is a flow chart showing an embodiment of the process of the present invention and is not meant to limit the subject matter as set forth in the claims.

DETAILED DESCRIPTION OF THE INVENTION

The present invention is described in more detail hereinbelow. Esters of acetic acid and 1,4-butanediol or 1,4-dihydroxybutene-2employed in the process of the invention include mono and di-acetic acid esters of above 1,4-glycols such as 1,4-diacetoxybutane, 1-hydroxy-4-acetoxybutane, 1,4-diacetoxybutene-2, 1-hydroxy-4-acetoxybutene-2. These esters may be produced in various known methods. For example, 1,4-diacetoxybutene-2, and 1-hydroxy-4-acetoxybutene-2separated from acetoxylation reaction products obtained by interacting butadiene, acetic acid and oxygen or an oxygen-containing gas in the presence of a palladium-based catalyst, may be used as a starting material of the process of the invention. Further, 1,4-diacetoxybutane, and 1-hydroxy-4-acetoxybutane obtained by hydrogenation of the acetoxylation reaction product may also be used.

The ester of acetic acid and a glycol employed in the process of the invention is mainly composed of the ester of 1,4-glycol exemplified above. The ester may contain isomers thereof such as acetic acid esters of 1,2- and 1,3-glycols, incorporated therein during its reaction or purification step. Further, the ester may contain butyl acetate, acetic acid and the like secondarily produced during hydrogenation step. It is preferred however, that the ester be composed of at least 99.5% of an acetic acid ester of 1,4-glycol.

1-Hydroxy-4-acetoxybutane can be produced by partial hydrolysis of 1,4-diacetoxybutane. However, it is suited to use 1-hydroxy-4-acetoxybutane obtained by a method including reacting propylene with molecular oxygen and acetic acid in the presence of a palladium catalyst to give allylacetate and subjecting allylacetate to an OXO-reaction to convert into 4-acetoxybutryaldehyde, followed by hydrogenation. In this case, contamination of 2-methyl-3-acetoxypropyl alcohol derived from 2-methyl-3-acetoxypropionaldehyde secondarily produced during the OXO-reaction stage, in the 1-hydroxy-4-acetoxybutane starting material does not adversely affect the operation of the present invention.

Regarding the other reactant for the cyclization reaction, water, while any feasible water may be used, it is preferred that the water contain no chloric ion.

The acid catalyst useful in the process of the present invention is a non-volatile acid which can form a liquid phase with the reactant under the reaction conditions. Illustrative of the catalysts are inorganic acids such as sulfuric acid, phosphoric acid and organic sulfonic acids such as benzenesulfonic acid, toluenesulfonic acid, trifluoromethanesulfonic acid. The use of sulfuric acid is most preferable economically. In practising the process of the invention, the starting ester and acid catalyst are fed to a reaction zone as a liquid phase while simultaneously introducing water thereinto to effect the cyclization reaction. The amount of the catalyst used varies according to the kinds of acid catalysts, but it is generally between 5 and 60% by weight, preferably between 7 and 40% by weight and more preferably between 10 and 30% by weight based on a total of the liquid phase in the reaction zone. The amount of water fed to the reaction zone is so controlled as to maintain the water content in the reaction zone in the range of generally between 1 to 60% by weight, preferably between 2 and 30% by weight and, more preferably between 5 and 20% by weight based on the total of the liquid phase in the reaction zone. It is preferred that water be fed to the reaction zone in the form of steam.

The cyclization reaction may be conducted in any manners as far as gas-liquid contact is desirably effected. For example, the following embodiment are suited:

(1) An acid catalyst is provided in a reactor of a bubble tower or a vessel equipped with a stirrer, to which a liquid ester of acetic acid and a glycol is fed while blowing thereinto water, especially steam. The reaction is carried out under a exterior heating conditions, if necessary. In the case of the bubble tower, perforated plates are preferably provided in the tower to partition inside the tower into a plurality of vertically spaced chambers. The liquid components are fed from the top of the tower while steam is fed from the bottom of the tower. Further, a plurality of such tower are preferably used to form a multi-stage reactor for the cyclization reaction, where the liquid components are fed as the downstream and steam as the upstream. In the case of the vessel equipped with a stirrer, a multiple of the vessels are suitably used in series to form a multi-stage reactor, into which the reactants are preferably introduced in the similar manner as in the bubble tower system. In this case, the catalyst may be either previously provided in each of the vessels or continuously fed together with the ester.

(2) A tower packed with a packing material made of metal or porcelain such as Raschig ring, berl saddle, Intalox saddle, is used as a reactor, into which the liquid ester and non volatile acid catalyst are introduced and to which steam is simultaneously fed to allow the reaction between the ester and water to proceed.

While it is possible to introduce both the liquid components and steam from either the top or the bottom of the tower and concurrently flow them downwardly or upwardly through the tower, it is suited to bring the liquid components into countercurrent contact with steam. In this case, the liquid components are preferably allowed to flow downwardly while flowing steam upwardly. Further, a plurality of such packed towers may be used to form a multi-stage reactor likewise in the case of (1) above.

In either embodiment, the reactor should be made of materials having sufficient resistance to the attack of acids. Hastelloy may be used at a temperature of somewhat higher than 100° C., and the reactor lined with glass may be used at more elevated temperatures. At any temperatures, the use of the glass lined reactor is preferable, because there will encounter no deposition problem of high boiling point substances to the wall of the reactor. The reaction is performed generally at a temperature of between 100 and 200° C. preferably between 120 and 160° C. The reaction pressure is generally between 300 mmHg and 3 Kg/cm$^2$ gauge, preferably between 500 mmHg and 1 Kg/cm$^2$ gauge.

The cyclic ether produced by the reaction described above is distilled off from the reaction zone as a gas phase, which is then transferred into a purifying system to recover the ether product in high quality.

According to the process of the invention, the distillation residue in the reaction zone is discharged therefrom and this residue is introduced into a solid-liquid separator. The residue contains unreacted acetic acid ester, acetic acid and cyclic ether (tetrahydrofuran or dihydrofuran) both produced by the reaction, the acid catalyst and high boiling point substances. The form of the high boiling point substances in the effluent varies depending upon the reaction conditions employed, particularly concentration of each of the components in the reaction mixture, especially of water and the reaction temperature. That is, when the reaction is performed at a high temperature and in the presence of large amount of water, the high boiling point substance are apt to solidify. Particularly, when the concentration of water in the reaction mixture is 40 or more % by weight, the high boiling point substances produced tend to change in the form of a slurry. Accordingly, the distillation residue as it is, may be subjected to the solid-liquid separation treatment. However, while the conversion rate of the acetic acid ester to the cyclic ether is higher as the amount of water is increased, too much presence of water is economically disadvantageous because the content of water in the gas phase of ether product becomes higher and necessitates the complex rectification to recover the ether free from water. Further, when the high boiling substances change in a solid form, it often causes some trouble in an operation of reaction such as the deposition thereof on the wall of the reactor. Thus, in a preferred embodiment, the amount of water is controlled within the afore-mentioned preferred range to minimize the solidification of the high boiling point substances during the reaction stage, and water is then added to the effluent from the reaction zone to effect the solidification. In case the solidification of the high boiling point substances is still insufficient, it is advantageous to heat the residue added with water at a temperature within a range from 130° C. to 60° C., preferably 110° C. to 80° C., because it serves to facilitate the production of solidified substances having larger particle sizes. The temperature of the residue from the reaction zone is dependent upon the reaction temperature employed. In some cases, the residue has a very high temperature and may cause a possible problem of deterioration of separation apparatuses. However, it is very difficult to select a suitable separation apparatus, particularly filtration apparatus which has sufficient deterioration resistance. For this reason, it is economically disadvantageous to subject such effluent having a high temperature to a separation treatment, as it is. Therefore, it is preferred that the temperature of the fully solidified high boiling point substances-containing slurry formed by the above-described treatment, be adjusted to a range of generally between 80 and 20° C., more preferably between 50 and 30° C. before introducing into the separator.

The residue is preferably first introduced into a slurry forming vessel before feeding to the separator. In the vessel, the effluent is mixed with water to make the water content in the resulting mixture in the range of between 95 and 20% by weight preferably between 90 and 30% by weight. By this, the high boiling point substances presented either in solution or suspension of fine particles in the residence are permitted to form coarse particles through flocculation and the like, so that the facility for filtration of the high boiling point substances is improved, ensuring easy separation operations. The filtration efficiency at the separation step is further increased by adding to the residue a separation accelerator so as to improve the filtration of the solidified high boiling point substances. Organic and inorganic materials having large surface area such as activated carbon, diatomaceous earth, active alumina, pulp, etc. are employed as the separation accelerator. The use of activated carbon is most preferably in view of its simplicity in handling after separation. The surface area (according to BET method) of the separation accelerator is generally between 100 and 1,200 m$^2$/g, preferably between 200 and 800 m$^2$/g.

The amount of the separation accelerator used is variable according to the amount and the state of particles of the high boiling point substances produced. Generally, the accelerator is added in such an amount that is required to render the solid content in the slurry after the addition in the range of between 30 and 1% by weight, preferably between 10 and 2% by weight. The particle size of the accelerator is generally between 10 and 200 mesh (Tyler), preferably between 50 and 100 mesh.

While a variety of apparatuses are available as the solid-liquid separator, a filter is generally employed in the process of the invention. Since tetrahydrofuran contained in the slurry to be treated is volatile, the filter is preferred to be a closed type. Cloth or porcelain is used as a filter medium. The solid-liquid separation is suitably conducted by a semi-batch method with the use of a closed type filter entirely lined with glass and furnished with a porcelain filter medium. The term "semi-batch method" herein is intended to mean a process wherein filtration is continuously carried out for a certain period of time, back washing is subsequently conducted to withdraw from the filter medium high boiling point substances-containing solids separated thereon and then the alternative filtration and backwashing operations are repeatedly performed.

The filtrate obtained by the solid-liquid separation contains the starting ester remained, cyclic ether, acid catalyst and water, and is recycled into the reaction zone.

A preferred embodiment of the process of the invention is hereinbelow described with reference to the accompanying drawing. In the Figure, designated by 11 is a reactor, 12 a slurry forming vessel, 13 a filter and 14 a storage tank.

To the reactor 11 provided with an aqueous solution containing an acid catalyst, a starting acetic acid ester is fed through a conduit 1 and, simultaneously, a filtrate is recycled through a conduit 8 when the process is in a steady state, thereby to effect the cyclization reaction. The reaction is carried out while maintaining the reaction temperature within a suitable range by flowing heated steam through a jacket of the reactor. Tetrahydrofuran produced by the reaction is distilled off as a mixed gas together with acetic acid and water. The mixed gas is subsequently introduced into a purifying system to recover tetrahydrofuran therefrom. The effluent from the reaction zone is introduced via conduit 3 into the slurry forming vessel 12. If desired, a treatment vessel may be provided before the slurry forming vessel. Water is fed to the slurry forming vessel to dilute the effluent so as to facilitate solidification of high boiling point substances. In this case, the solidification efficiency may be improved by adding a separation accelerator in combination with water. The temperature of the mixture in the slurry forming vessel is controlled by flowing cooling water through a jacket of the vessel.

Slurry discharged from the slurry forming vessel is introduced into the filter 13 via conduit 5, where the slurry is separated into a solid phase containing the high boiling point substances and a filtrate. When the separation is conducted by a semi-batch method described above, it is possible to effect the separation continuously as a whole by providing a plurality of separators in parallel and to use the separators alternatively. The filtrate is introduced into the storage tank 14 through a conduit 6, a portion of which is fed to the reactor through the conduit 8 while controlling its flow rate by means of a pump. By recycling the filtrate into the reactor, since the filtrate contains, in addition to the unreacted acetic acid ester, the acid catalyst and water including the all the water additionally supplied at the slurry forming vessel, it is sufficient to add a fresh catalyst and water to the reactor each in an amount required to make up for the amount lost during filtration step and the like, to maintain the overall process in a steady state. As is understood from the foregoing, in accordance with the process of the present invention, the high boiling point substances secondarily produced during the cyclization reaction can be solidified by a simple manner and taken out from the system. Further, water used to effect the solidification is advantageously reused as a starting material for the reaction. The following example will further illustrate the process of the invention. However, the present invention may be embodied in other forms without departing from the essential characteristics thereof.

EXAMPLE 1

The reaction was conducted using the system illustrated in the accompanying drawing.

As a reactor, 50 liter reaction vessel lined with glass, equipped with a stirrer and provided with a jacket for steam-heating was used. The temperature in the reactor was maintained at 130° C. under atmospheric pressure by flowing through the jacket heated steam while controlling its pressure. To the reactor, 1,4-diacetoxybutane was fed through the conduit 1 at a feed rate of 0.766 Kg/h while simultaneously introducing thereinto the recycling filtrate through the conduit 8 at a feed rate of 0.317 Kg/h, thereby to allow the reaction to proceed.

The gas containing tetrahydrofuran was distilled off from the top of the reactor through the conduit 2 at a rate of 0.87 Kg/h. The distillate was found to contain 36.6% by weight of tetrahydrofuran, 3.6% by weight of water and 60.7% by weight of acetic acid.

The residual liquid was discharged from the lower section of the reactor through the conduit 3 at a rate of 0.213 Kg/h, which contained 3.3% by weight of the high boiling point substances in addition to unreacted 1,4-diacetoxybutane, acetic acid and sulfuric acid, and was entirely introduced into the slurry forming vessel.

The slurry forming vessel was lined with glass and had the inner volume of 50 liter. A stirrer and a jacket were provided thereto. The inside the vessel was maintained at 40° C. by flowing through the jacket cooling water while controlling its flow rate. To the vessel, water containing 11.1% by weight of activated carbon powder (BET method: surface area of 1,000 m$^2$/g) was fed in the form of a slurry at a feed rate of 0.126 Kg/h through the conduit 4.

The slurry containing activated carbon to which the high boiling point substances were adsorbed and having the composition shown below, was introduced into the filter through the conduit 5 at a feed rate of 0.338 Kg/h. The composition of the slurry was as follows:

| | |
|---|---|
| Tetrahydrofuran | 6.5 wt. % |
| Water | 34.0 wt. % |
| Acetic acid | 32.0 wt. % |
| 1,4-Diacetoxybutane | 15.4 wt. % |
| High boiling point substances | 2.1 wt. % |
| Activated carbon | 4.1 wt. % |
| Sulfuric acid | 5.9 wt. % |

The filter was a Nutsche made of porcelain and having an inner diameter of 50 cm. As a filter medium, filter cloth made of a polyester was employed. The Nutsche had a closed upper end. The filtrate was discharged from the filter and introduced into the storage tank through the conduit 6 at a rate of 0.317 Kg/h. As described above, the filtrate in the tank was recycled into the reactor through the conduit 8 at a feed rate of 0.317 Kg/h. The foregoing process was continued for 100 hours. As a result, 2,700 Kg (dried state) of solid were collected which were separated by the filter.

What I claim is:

1. In a process for the production of a cyclic ether by reacting an ester of acetic acid and 1,4-butanediol or 1,4-dihydroxybutene-2 with water in the presence of a nonvolatile acid catalyst, the improvement comprising:
    (a) simultaneously feeding said ester and said acid catalyst as a liquid and an amount of water necessary to form a first mixture having a water content of between about 2 and 30% by weight into a reaction zone to thereby produce said cyclic ether as a gas and a residue containing unreacted ester, acid catalyst and a high boiling point substance as a liquid,
    (b) distilling off said cyclic ether and removing said residue from said reaction zone,
    (c) mixing said residue with an amount of water necessary to provide a second mixture having a water content of between about 30 and 90% to thereby form a suspension containing solid particles of said high boiling point substance,
    (d) introducing said suspension into a solid-liquid separation zone to separate said suspension into a liquid phase portion and a solid phase portion, and
    (e) recycling said liquid phase portion to said reaction zone and withdrawing said solid phase portion from said separation zone.

2. The process of claim 1 further comprising subjecting said second mixture to a heat treatment and introducing said heat treated mixture into said separation zone.

3. The process of claim 2 wherein said solid-liquid separation zone is maintained at a temperature of between about 20° C. and 80° C.

4. The process of claim 3 wherein said temperature is between about 30° C. and 50° C.

5. The process of claim 1 wherein said ester is acetic acid diester of 1,4-butanediol and said cyclic ether is tetrahydrofuran.

6. The process of claim 1 wherein said acid catalyst is sulfuric acid.

7. The process of claim 1 wherein said first mixture has a water content of between about 5 and 20% by weight.

8. In a process for the production of a cyclic ether by reacting an ester of acetic acid and 1,4-butanediol or 1,4-dihydroxybutene-2 with water in the presence of a nonvolatile acid catalyst, the improvement comprising:
    (a) simultaneously feeding said ester and said acid catalyst as a liquid and an amount of water necessary to form a first mixture having a water content of between about 2 and 30% by weight into a reaction zone to thereby produce said cyclic ether as a gas and a residue containing unreacted ester, acid catalyst and a high boiling point substance as a liquid,
    (b) distilling off said cyclic ether and removing said residue from said reaction zone,
    (c) mixing said residue with a separation accelerator and an amount of water necessary to produce a second mixture having a water content of about between 30 and 90% to thereby form a suspension containing solid particles of said high boiling point substance,
    (d) introducing said suspension into a solid-liquid separation zone to separate said suspension into a liquid phase portion and a solid phase portion, and
    (e) recycling said liquid phase portion into said reaction zone and withdrawing said solid phase portion from said separation zone.

9. The process of claim 8 wherein said separation accelerator has a surface area in a range of from 100 to 1200m$^2$/g.

10. The process of claim 9 wherein said range is from 200 to 800m$^2$/g.

11. The process of claim 8 wherein said separation accelerator is selected from the group consisting of activated carbon, diatomaceous earth, active alumina, and pulp.

12. The process of claim 11 wherein said separation accelerator is activated carbon.

13. The process of claim 8 wherein said separation accelerator has a particle size in a range of from 10 to 200 mesh.

14. The process of claim 13 wherein said range is from 50 to 100 mesh.

15. The process of claim 8 further comprising mixing said residue with said separation accelerator in an amount necessary to provide an amount of said solid particles in said suspension of between about 1 and 30% by weight and introducing said suspension into a solid-liquid separation zone maintained at a temperature of between about 20° C. and 80° C. to thereby separate said suspension into said liquid phase portion and said solid phase portion.

16. The process of claim 15 wherein said amount of said solid particles in said suspension is between about 2 and 10% by weight.

17. The process of claim 8 wherein said ester is acetic acid diester of 1,4-butanediol and said cyclic ether is tetrahydrofuran.

18. The process of claim 8 wherein said acid catalyst is sulfuric acid.

19. The process of claim 8 wherein said first mixture has a water content of between about 5 and 20% by weight.

* * * * *